(12) United States Patent
Sheedy et al.

(10) Patent No.: US 11,610,512 B2
(45) Date of Patent: Mar. 21, 2023

(54) EXPIRATORY BREATHING SIMULATOR DEVICE AND METHOD

(71) Applicants: Michael Bernard Arthur Sheedy, Christchurch (NZ); Daniel Hartwell, Christchurch (NZ)

(72) Inventors: Michael Bernard Arthur Sheedy, Christchurch (NZ); Daniel Hartwell, Christchurch (NZ)

(*) Notice: Subject to any disclaimer, the term of this patent is extended or adjusted under 35 U.S.C. 154(b) by 1125 days.

(21) Appl. No.: 16/230,319

(22) Filed: Dec. 21, 2018

(65) Prior Publication Data

US 2020/0168125 A1 May 28, 2020

(51) Int. Cl.
G09B 23/28 (2006.01)
A61B 5/08 (2006.01)
A61M 16/00 (2006.01)

(52) U.S. Cl.
CPC .......... *G09B 23/288* (2013.01); *A61B 5/0816* (2013.01); *A61B 5/082* (2013.01); *A61M 16/024* (2017.08)

(58) Field of Classification Search
CPC .... G09B 23/288; G09B 23/28; A61B 5/0816; A61B 5/082; A61M 16/024; A61M 16/022; A61M 2202/0225; A61M 2205/502

USPC .......................................................... 434/265
See application file for complete search history.

(56) References Cited

U.S. PATENT DOCUMENTS

| | | | |
|---|---|---|---|
| 9,277,890 B2 | 3/2016 | Syroid et al. | |
| 2009/0107494 A1* | 4/2009 | Freitag | A61M 16/00 128/207.14 |
| 2013/0259744 A1* | 10/2013 | Yoshida | A61M 1/0281 422/44 |
| 2013/0317837 A1* | 11/2013 | Ballantyne | A61M 1/34 705/2 |
| 2015/0328403 A1* | 11/2015 | Dobbies | A61B 5/7278 600/364 |
| 2016/0184518 A1* | 6/2016 | Freeman | A61M 5/1723 604/503 |

* cited by examiner

*Primary Examiner* — Tanmay K Shah
(74) *Attorney, Agent, or Firm* — Fish & Richardson P.C.

(57) ABSTRACT

An Expiratory breathing simulator device is provided and configured to simulate a real patient's End Tidal $CO_2$ ($ETCO_2$). The device is configured to be used with a vital signs simulator to simulate a patient's behaviour on a medical monitoring apparatus, for example for training medical professionals.

13 Claims, 10 Drawing Sheets

EXPIRATORY BREATHING SIMULATOR DEVICE AND METHOD

BACKGROUND OF THE DISCLOSURE

Field of the Disclosure

The present disclosure generally relates to an expiratory breathing simulator device and method for simulating the expiratory breathing phase of a patient. In some aspects, such a device and method can be used with a medical simulation system for simulating aspects of a patient during anaesthesia, for training purposes.

Description of the Related Art

It is known to provide a medical simulation system configured to simulate aspects of a patient, and in particular aspects of the patient's physiological output or vital signs. An example of such a system is the ProSim 8 Vital Sign and ECG Patient Simulator™ provided by Fluke Corporation. Such a system simulates aspects of a patient's physiological output, such as vital signs, such that the system can interact with other patient monitoring equipment and simulate the patient interacting with such other patient monitoring equipment. This simulator is used to test and calibrate vital signs monitoring equipment used in hospitals, and can be used for training medical practitioners.

We have developed a simulator, comprising simulator software and a GUI, configured to interact with a vital sign simulator as above, to enable scenarios replicating actual patient behaviour to be run through the vital sign simulator, such as the ProSim 8, and which allows anaesthetists to train on the patient monitoring equipment used in hospitals. Our Simulator software and GUI can be used with an off-the-shelf ProSim 8, with no modification to the ProSim 8 or its software required.

A medical simulation system comprising our simulator software and GUI and a vital sign simulator can be used to train medical personnel without requiring a real patient in situ. This enables a medical practitioner to test the medical equipment, and receive training on how to use that medical equipment, without requiring a patient to be present. Patient physiological outputs that a typical vital sign simulator can simulate include ECG (including fetal ECG/IUP and arrhythmias), respiration, temperature, IBP/cardiac catheterization, cardiac output, NIBP, and $SpO_2$.

Simulation can be an interactive educational and training tool used to build confidence, improve clinical knowledge and enhance team performance through practice. Such simulation can be of particular use in anaesthesiology which is a hands-on medical specialty and, as in other hands-on medical specialties, an effective way to improve a skill is to practice it repeatedly. In anaesthetics, simulation provides a safe learning environment where consultants, registrars, technicians and students can be taught, practice and be evaluated without putting a real patient at risk.

Low priced simulators exist but they can lack simulation quality. Higher quality (termed "high-fidelity") simulators are available but they can cost in excess of US$100,000 and can lack key features that the anaesthetist community might desires.

Feedback from practitioners internationally has identified that the full value of such a simulation system would not be realised without improvements to generate End Tidal CO2 ($ETCO_2$), an important vital sign of the patient.

An $ETCO_2$ signal consists of both a waveform and a specific value, both of which are important for high-fidelity simulation. As used herein, $ETCO_2$ is used to refer to both the expiratory waveform, and the specific $ETCO_2$ value, as appropriate.

In anaesthesia, $ETCO_2$ is typically directly measured by the anaesthetic machine or a specific module attached to clinical monitors and is therefore not emulated by the ProSim8 or any other emulator. For simulators using a computer-generated monitor, the $ETCO_2$ trace can be generated. However, when using real clinical monitors, it is much more difficult because they are measuring gas concentration. For example, the relatively expensive METI-HPS system requires an underfloor piped gas supply, introducing further installation and maintenance costs. The CAE Human Patient Simulator (HPS) is a manikin produced by CAE which emulates a human by simulating how a patient would exchange gases. To do this the HPS needs to be able to be plumbed into a gases supply to simulate the lungs gas exchange with real volumes.

A typical $ETCO_2$ waveform in a real, spontaneously breathing patient, might look like the waveform shown in FIG. 8a. Such a waveform is well understood, but primarily comprises an initial upslope, a relatively flat expiratory plateau, a peak end tidal $ETCO_2$ value being the peak point at the end of the expiratory plateau, and a final downslope being the beginning of the inspiratory phase.

It can be difficult to accurately emulate $ETCO_2$ across the entire $ETCO_2$ waveform. It is important that $ETCO_2$ is accurately emulated, to ensure that the overall simulation of a patient's response is representative of a real patient.

SUMMARY OF THE DISCLOSURE

It is an object of the present disclosure to provide an expiratory breathing simulator device and method for simulating the expiratory breathing phase of a patient that can accurately replicate a patient's $ETCO_2$, and/or a medical simulation system that will at least provide the public or the medical profession with a useful choice.

Whilst primarily designed for use in the training of anaesthetists, the an breathing simulator device and method, and any medical simulation system with which it is used, is equally applicable to many other areas of healthcare and such as, for example, obstetric, nursing and ICU simulations.

Accordingly in one aspect the disclosure may broadly be said to consist in an expiratory breathing simulator device configured to simulate a real patient's expiratory breathing phase, the device comprising a housing comprising:
 a) a $CO_2$ inlet configured to receive $CO_2$ from a $CO_2$ source;
 b) a $CO_2$ outlet from which a $CO_2$ flow exits the housing, the $CO_2$ outlet being configured to be connected to a medical monitoring apparatus;
 c) a $CO_2$ flow path through the housing from the $CO_2$ inlet to the $CO_2$ outlet;
 d) at least one sensor configured to measure a property of the $CO_2$ in the housing;
 e) a $CO_2$ adjuster configured to control the pressure and/or flow rate of $CO_2$ in the flow path using an output signal from the sensor,
 f) an air pump configured to deliver air into the flow of $CO_2$ in the flow path; and
 g) a controller configured to control the adjuster to control the $CO_2$ flow output from the $CO_2$ outlet such that the $CO_2$ flow has a desired or predetermined waveform;

wherein the controller also controls the air pump to selectively deliver air into the $CO_2$ flow to prevent a value of $ETCO_2$ being significantly greater than zero during inspiration.

The simulator device may comprise a $CO_2$ regulator configured to reduce the pressure of the $CO_2$ from the $CO_2$ source.

The sensor may comprise a pressure sensor.

The $CO_2$ adjuster may comprise a proportional valve.

The sensor may comprise, or additionally comprise, a flow sensor or flow meter configured to generate an output indicative of the flow rate of the $CO_2$ flow in the $CO_2$ flow path.

The controller may comprise one or more electronic data processors, and a wireless transceiver, configured to receive a $CO_2$ control signal from a further electronic device.

The housing may be oblong and comprise a recessed portion on which the following connectors are provided, such that the connectors are recessed from the exterior of the housing:
- a) a $CO_2$ input connector for connection to the $CO_2$ source; and
- b) a $CO_2$ output connector for connection to a patient monitor or other medical device.

The simulator device may comprise:
- a) an ambient air inlet; and/or
- b) an oxygen inlet, for optional connection to an oxygen supply.

The device housing may comprise any one or more of:
- a) a $CO_2$ pressure indicator, indicative of sufficient pressure being provided by the $CO_2$ source;
- b) a connection indicator, indicative of the strength of any wireless connection with a remote electronic device;
- c) a battery indicator, indicative of the charge state of the battery;
- d) a power button, to activate or deactivate the device;
- e) a $CO_2$ gauge.

According to another aspect of the disclosure there is provided a medical simulation system comprising:
- a) the simulator device according to any one of the above statements,
- b) a vital signs simulator configured to simulate other vital signs of a patient; and
- c) a simulation controller;

wherein the simulation controller is configured to generate a $CO_2$ control signal used by the simulator device to control the waveform of the $CO_2$ flow generated by the simulator device.

The system may comprise a user interface configured to enable a user to adjust the $CO_2$ control signal.

The user interface may comprise a graphic user interface.

According to a further aspect of the disclosure there is provided an expiratory breathing simulator method configured to simulate a real patient's expiratory breathing phase, the method comprising steps of:
- a) receiving $CO_2$ in an inlet of an expiratory breathing simulator device from a $CO_2$ source;
- b) controlling the pressure of $CO_2$ in a flow path through the device using a $CO_2$ adjuster of the device;
- c) delivering a controlled flow of air into the flow of $CO_2$ in the flow path using an air pump;
- d) using a controller to control the $CO_2$ adjuster to control the $CO_2$ flow output from a $CO_2$ outlet of the device to generate a $CO_2$ flow having a desired or predetermined waveform;
- e) using a controller to control the air pump to deliver air into the $CO_2$ flow to prevent a value of $ETCO_2$ being significantly greater than zero during inspiration.

Further aspects of the disclosure, which should be considered in all its novel aspects, will become apparent from the following description.

DESCRIPTION OF THE DRAWINGS

A number of embodiments of the disclosure will now be described by way of example with reference to the drawings in which.

DETAILED DESCRIPTION OF SPECIFIC EMBODIMENTS

This disclosure relates to an expiratory breathing simulator device and method, that simulates a real patient's $ETCO_2$. The expiratory breathing simulator device generates an output signal in the form of a simulated $ETCO_2$ waveform which is fed directly into patient monitoring equipment. The combination of the expiratory breathing simulator device and the vital signs simulator generate a comprehensive vital signs simulation, which can be input into further patient monitoring equipment to generate a real-world training and education environment for medical practitioners.

Figure 1:
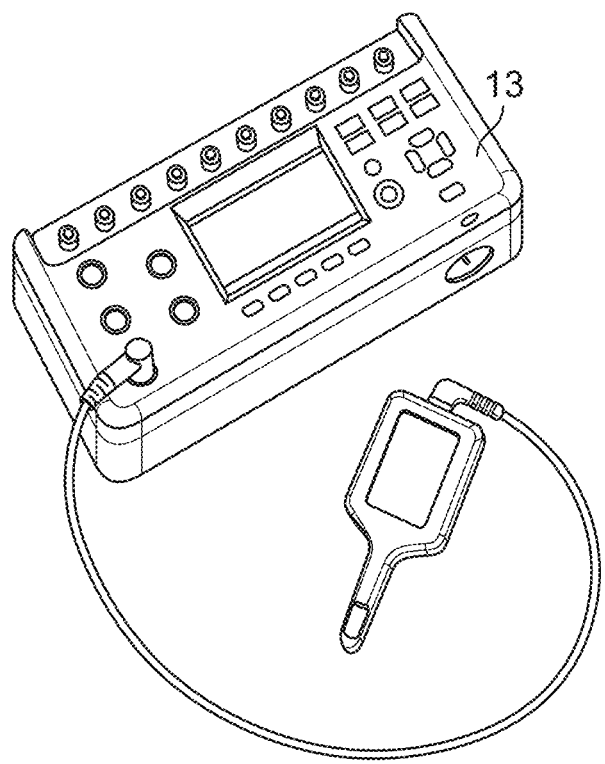
FIG. 1 is a perspective view of a vital signs simulator being the ProSim 8 medical simulation system of Fluke Corporation.
Figure 2:
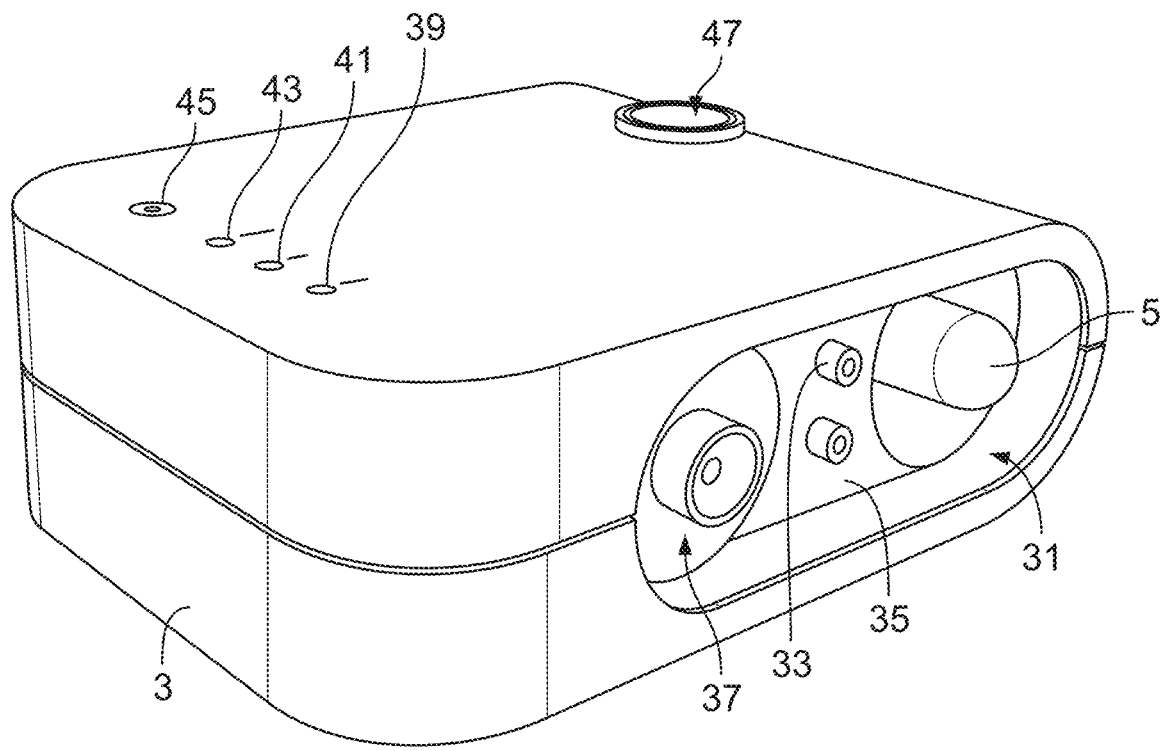
FIG. 2 is a perspective view of expiratory breathing simulator device in accordance with the present disclosure.
Figure 3:
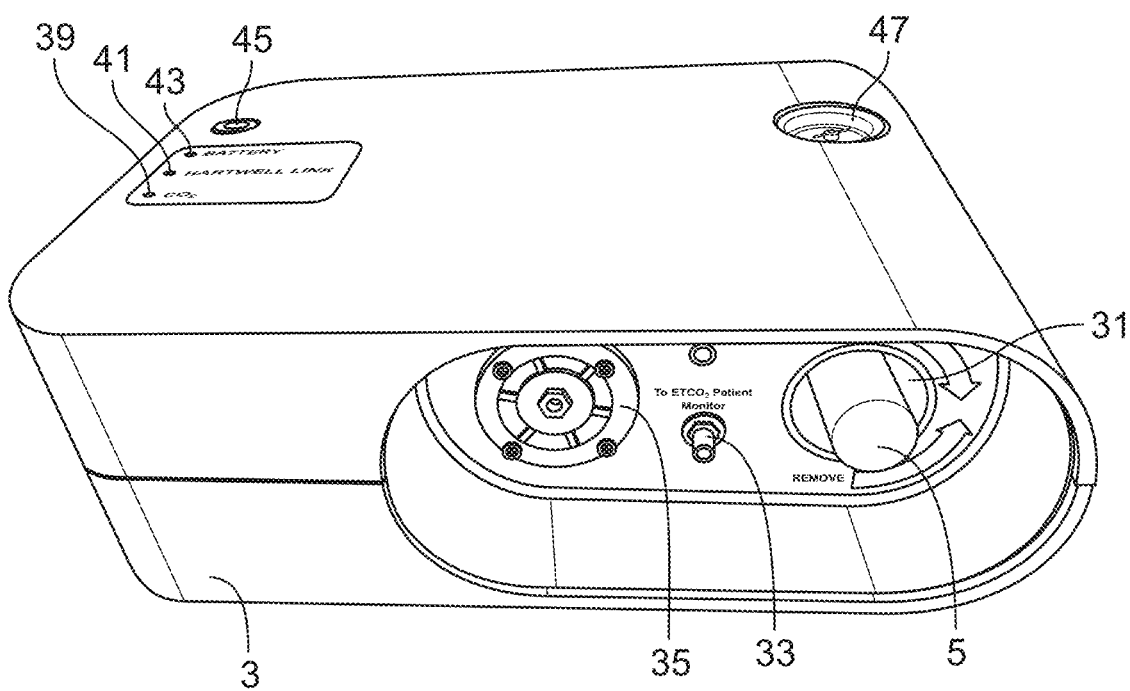
FIG. 3 is another perspective view of the device of FIG. 2.

The expiratory breathing simulator device 1 comprises an interface housing 3, for example as shown in FIGS. 2 and 3, configured to:
- a) receive $CO_2$ from a $CO_2$ source 5
- b) regulate the pressure of the $CO_2$ using a regulator 6;
- c) measure and control the pressure of the received $CO_2$ using a pressure sensor 7 and proportional valve 9,
- d) measure and control the $CO_2$ flow output from the proportional valve 9 using a flow sensor/meter 11 to generate a $CO_2$ flow having a desired or predetermined waveform and amplitude based on the patient monitor flow measured using a flow sensor/meter (number to be determined);
- e) selectively deliver a controlled flow of air into the $CO_2$ flow using an air pump 12;

f) output the $CO_2$ flow of the desired or predetermined waveform.

Figure 4:
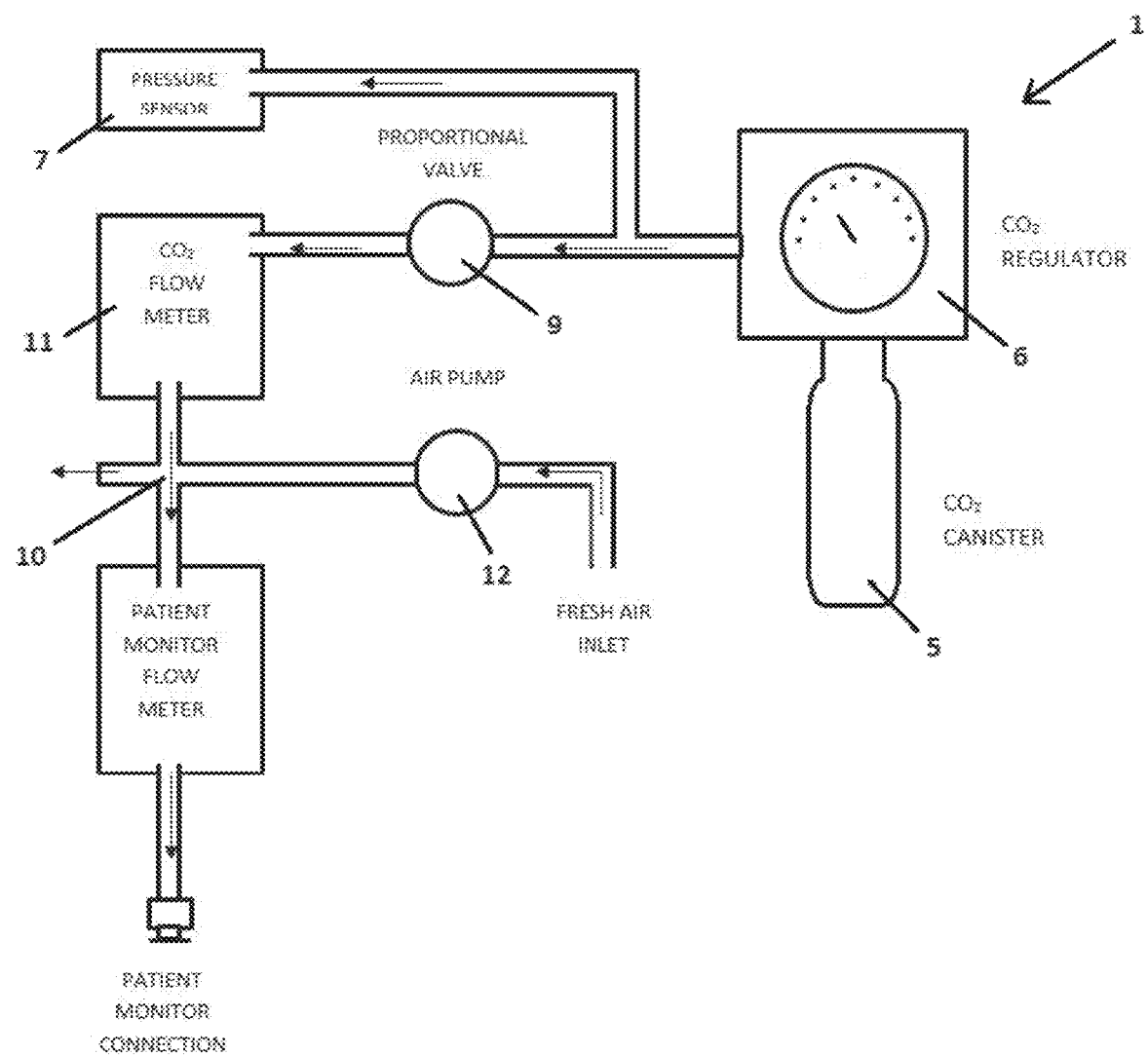
FIG. 4 is a drawing of the pneumatic flow path of an expiratory breathing simulator device and medical simulation system in accordance with this disclosure.

The output at f) can be delivered to patient monitoring equipment 8, to add an accurate representation of a patient's $ETCO_2$ to the vital signs data output to the device 8 by the vital signs simulator 13. These steps are broadly shown in schematic form in FIGS. 4 and 5.

The housing 3 thus comprises various $CO_2$ and inlet air flow path components, and an $ETCO_2$ controller 14 configured to control the flow path components to generate the desired or predetermined $CO_2$ waveform.

Figure 5:
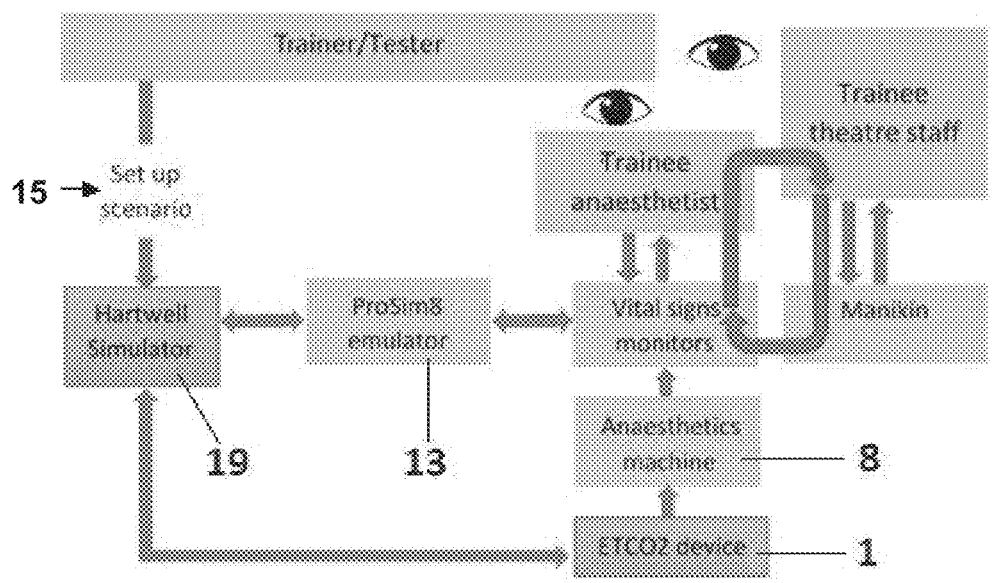
FIG. 5 is a schematic of a medical simulation system comprising the ProSim 8 and the device of FIGS. 2 and 3.

With reference to FIG. 5, the expiratory breathing simulator device 1 can be used with, and can comprise a removable or integral part of, a broader vital signs simulation system 15. System 15 comprises, in this example, expiratory breathing simulator device 1, a vital signs emulator 13 (such as the ProSim 8 described above), and a vital signs simulator controller and interface 19.

We provide a simulator controller comprising tablet-enabled software that implements the communication protocols of the ProSim8 emulator 17. Our software connects wirelessly to the ProSim8 and also links to vital signs monitoring equipment. Our simulator software works with a graphical user interface (GUI) which enables the operator to set up and change a training scenario relatively quickly and observe its progress at a glance.

Our simulator controller 19:
  Provides high-fidelity simulation at a fraction of the price of existing options.
  Enables quick and easy set-up of a wide range of critical event scenarios.
  Enables training using the specific vital signs monitoring equipment employed day-to-day by trainees, with their often-unique sounds and alarm states. Most highly priced simulators do not.
  Can be used within an actual operating theatre and is easily transferrable between operating theatres. This is not possible with most highly priced simulators.
  Greatly enhances the use of low fidelity manikins that healthcare providers already own.
  Can be utilized in a diverse range of training environments.
  Existing owners of vital sign simulators, such as a ProSim8, can secure a high-fidelity simulator for a modest additional investment.

Overview of Expiratory Breathing Simulator Device

This disclosure relates to an expiratory breathing simulator device configured to be an $ETCO_2$ simulator, to work with and be an addition to a medical simulation system 15 comprising a vital signs simulator 17, such the ProSim 8, and our simulator controller 19 (comprising our software and GUI), that enables $ETCO_2$ to also be simulated. We have determined that this additional vital signs simulation is important in accurately replicating a patient during testing and training.

We propose providing a separate expiratory breathing simulator device 1 that integrates into such a system 15, and in particular with our simulator controller 19.

$CO_2$ from a pressurised source 5 (for example such as a soda stream cylinder or bicycle tyre inflator cartridge) is released via a proportional valve 9 into a $ETCO_2$ gas sampling line 10 at appropriate concentrations and timings to replicate the actual $ETCO_2$ figure and trace on the monitor. This is controlled by the simulator software of controller 19 for emulating spontaneous breathing of a patient.

The device 1 works with $ETCO_2$ side stream sampling devices typically found in anaesthesia and emergency departments. The device 1 simulates a patient's $CO_2$ output when breathing by injecting small amounts of $CO_2$ into the clinical monitor's sampling line 10. The $CO_2$ source may be from a standard 25 g $CO_2$ cylinder. The amount of $CO_2$ released in the sampling line 10 is controlled by a proportional valve 9 which is in a closed loop system where flow is monitored to keep the $CO_2$ output stable.

Patient monitor $ETCO_2$ sampling devices are very sensitive and any small amount of $CO_2$ remaining in the sample line can increase the inspiration $ETCO_2$ value. Oxygen, from ambient air pumped by air pump 12, is then mixed in to allow flushing/purging of the residual $CO_2$ in the flow path to enable the inspiratory value to fall to zero. The oxygenated number on the, for example, anaesthetic machine, stays, or should stay, substantially the same.

The device 1 communicates with the simulator software controller 19 using, in this example, WiFi signals so is completely wireless. The device 1 can be powered by a suitable battery power source, such as Sealed Lead Acid (SLA), to make the device 1 portable and easy to connect.

Operation Overview

The device 1 is a wirelessly controlled device that simulated a real patient's $ETCO_2$ breathing pattern. The device 1 is controlled via software on a portable electronic device, such as a tablet, which allows for changes in Respiration Rate (RR), $ETCO_2$ Expiratory Plateau level and, in this example, four different shaped waveforms. The waveforms are for a patient who is ventilated, has mild and severe bronchospasm and also spontaneous breathing, examples of these four conditions being shown in FIGS. 8b-8e.

The $CO_2$ from the $CO_2$ canister source 5 screws into a $CO_2$ regulator 6. The regulated $CO_2$ is then controlled by a proportional valve 9 which is controlled to create the $CO_2$ waveform. The regulated $CO_2$ pressure is measured as a closed loop control of the $CO_2$ valve to ensure the correct flow level is maintained, the closed loop control using a signal indicative of the flow and or pressure of the $CO_2$, generated by flow meter 11 and/or pressure sensor 7. The $CO_2$ waveform is controlled in firmware by a closed loop system measuring the flow emitting from the proportional valve 9. The ratio of the patient monitor flow measured at flow meter 18 and the $CO_2$ flow determines the $ETCO_2$ Expiratory Plateau. In device 1, the proportional valve 9 is controlled by a voltage representative of the desired $CO_2$ output waveform. The proportional valve 9 then opens accordingly to create the $ETCO_2$ value based on the ratio of the patient monitor flow rate and the $CO_2$ flow rate.

On the inspiratory breathing phase the proportional valve 9 is closed, stopping any regulated $CO_2$ emitting. However, any $CO_2$ left in the flow path downstream from the proportional valve 9 can still be sucked into the patient monitor. This causes the inspiratory $ETCO_2$ value to be greater than 0 mmHg. An air pump 12 is utilised to blow any remaining $CO_2$ away from the patient monitor causing the Inspiratory $ETCO_2$ value to desirably fall to zero.

Housing/Enclosure

An example device housing/enclosure 3 can be seen in FIGS. 2 and 3 and incorporates the pressure sensor 7, proportional valve 9, flow meter 11, air pump 12, patient monitor flow meter 18 and $ETCO_2$ flow path conduit/tubing. The enclosure 3 further incorporates the $ETCO_2$ device controller, which may include one or more electronic data processors, and a WIFI wireless transceiver. Note that the devices 1 of FIGS. 2 and 3 are different, in that the device 1 of FIG. 2 includes an optional supplementary oxygen source inlet. If a supplementary oxygen source is used, an oxygen and $CO_2$ mixer 16 can be provided to mix these two gases prior to delivery to the medical monitoring apparatus 8.

The device enclosure 3 comprises connectors on a rear face, including:
 a) a $CO_2$ input connector 31 for connection to the $CO_2$ source 5—in this example, the $CO_2$ canister fits inside connector 31 so as to be retained partially inside the enclosure so as not to project beyond the periphery of the enclosure;
 b) a $CO_2$ output connector 33 for connection to a patient monitor or other medical device;
 c) an ambient air inlet 35;
an optional oxygen inlet 37, for optional connection to an oxygen supply;

The device enclosure also comprises, in this example, indicia and controls, including:
 a) a $CO_2$ pressure indicator 39, comprising a LED indicative of sufficient pressure being provided by the source 5;
 b) a connection indicator 41, comprising a LED indicative of the strength of any wireless connection with the controller 19;
 c) a battery indicator 43, comprising a LED indicative of the charge state of the battery;
 d) a power button 45, used to activate or deactivate the device 1;
 e) a $CO_2$ gauge 47.

The enclosure 3 further comprises ergonomic features to promote easy and safe use. The enclosure 3 comprises a recessed bulkhead 49 on which the $CO_2$ canister 5 and the patient monitor connection 33 are protected from accidental knocking and damage. There is also provided an analogue $CO_2$ gauge positioned on the top of the enclosure to enable easy viewing when screwing in a new canister to ensure it is fully seated.

The $CO_2$ regulator 6, and/or the proportional valve 9 are used to step down the very high $CO_2$ pressure in the canister source 5 from in excess of 1200 psi to a significantly lower pressure in the order of tens of psi.

Using real clinical monitors offers real advantages in simulation. It makes it more realistic for simulation participants, ensure the alarm triggers and noises used in simulation match those in clinical practice, and makes it far simpler to run simulations 'in-situ' in real healthcare environments. The controller 19 and device 1 allow easy control of real clinical monitors without the need for an expensive integrated manikin. Further, the device 1 provides accurate $ETCO_2$ waveform to be generated and used in the simulation. The controller 19 is the component that converts the $CO_2$ waveform output from device 1 to be generated as a $CO_2$ trace on a real clinical monitor.

Figure 6:
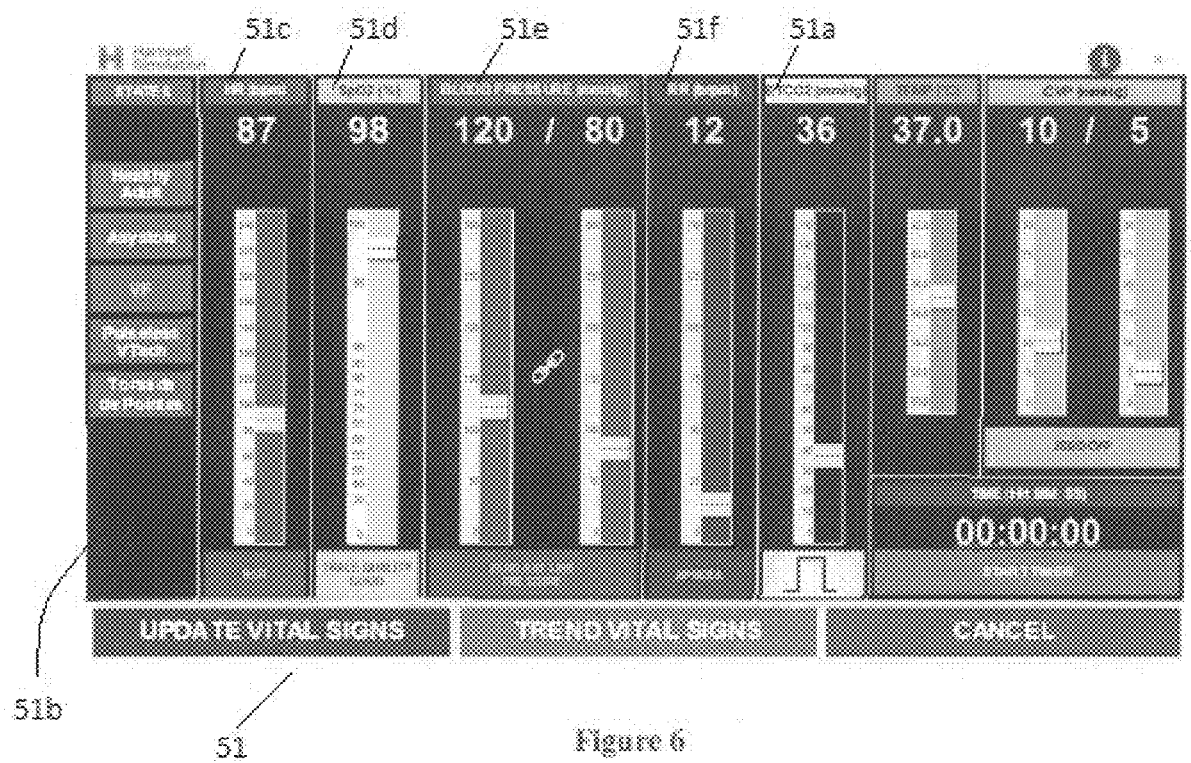
FIG. 6 is a GUI of a controller of the medical simulation system of FIG. 5.
Figure 7:
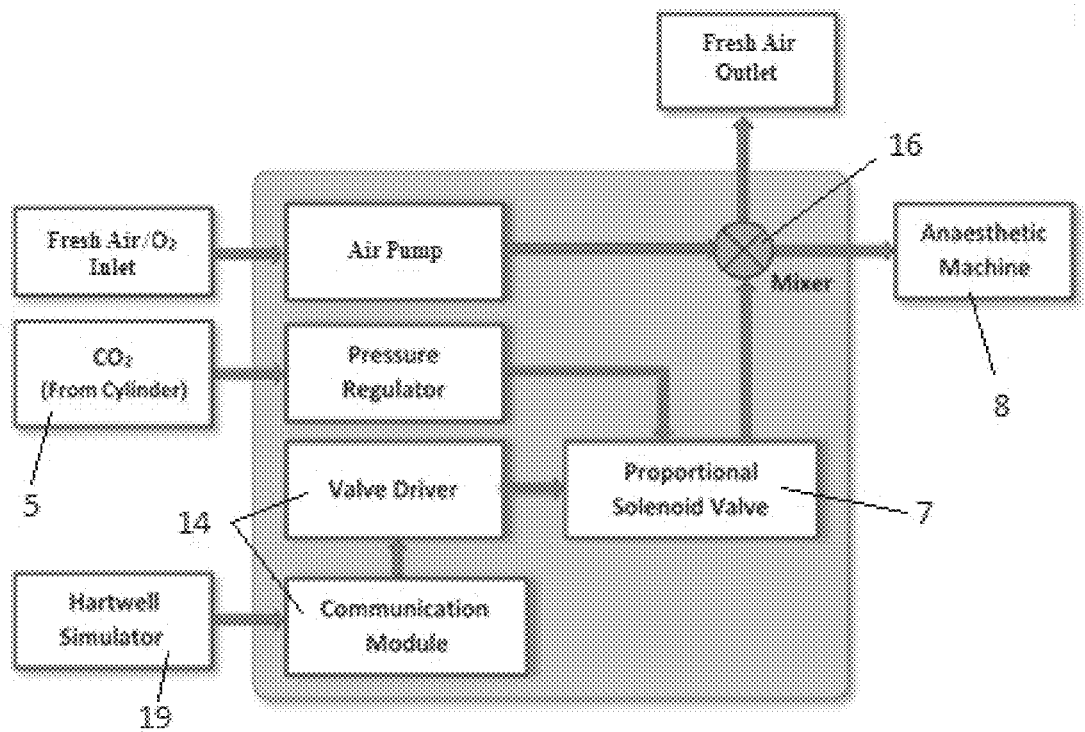
FIG. 7 is a schematic of part of a medical simulation system of FIG. 5.
Figure 8A:
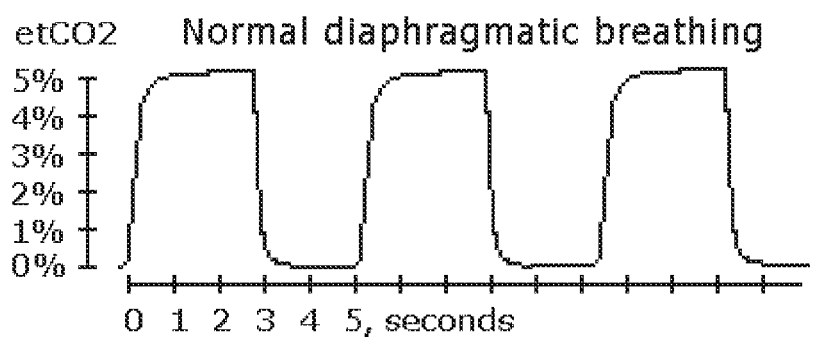
FIGS. 8a to 8e are images of waveforms from a standard patient monitoring equipment, in this example an anaesthetic machine, for a patient breathing normally, a ventilated patient, a spontaneously breathing patient, a patient having mild bronchospasm, and a patient having a severe bronchospasm, respectively.
Figure 8B:
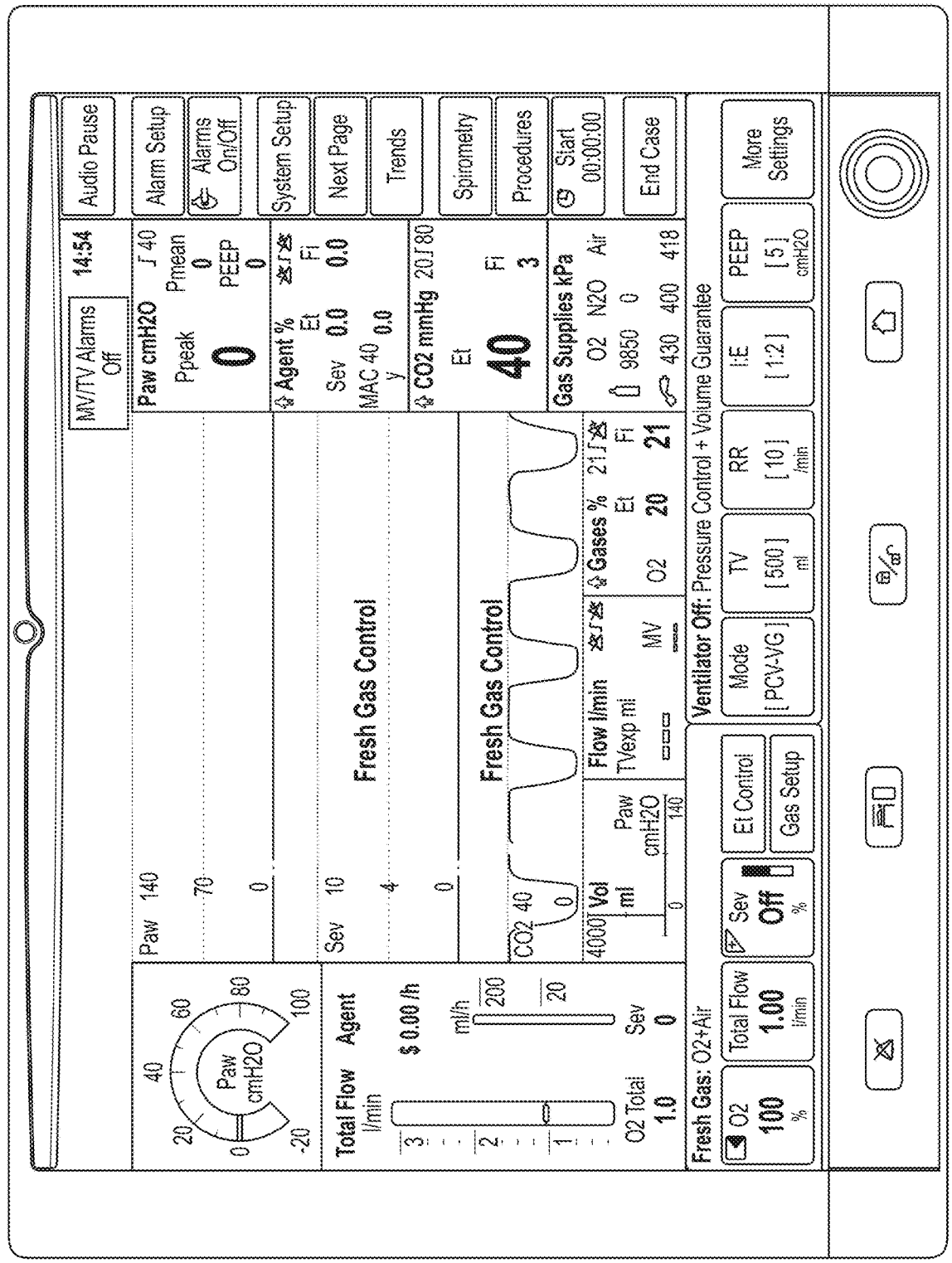
Figure 8C:
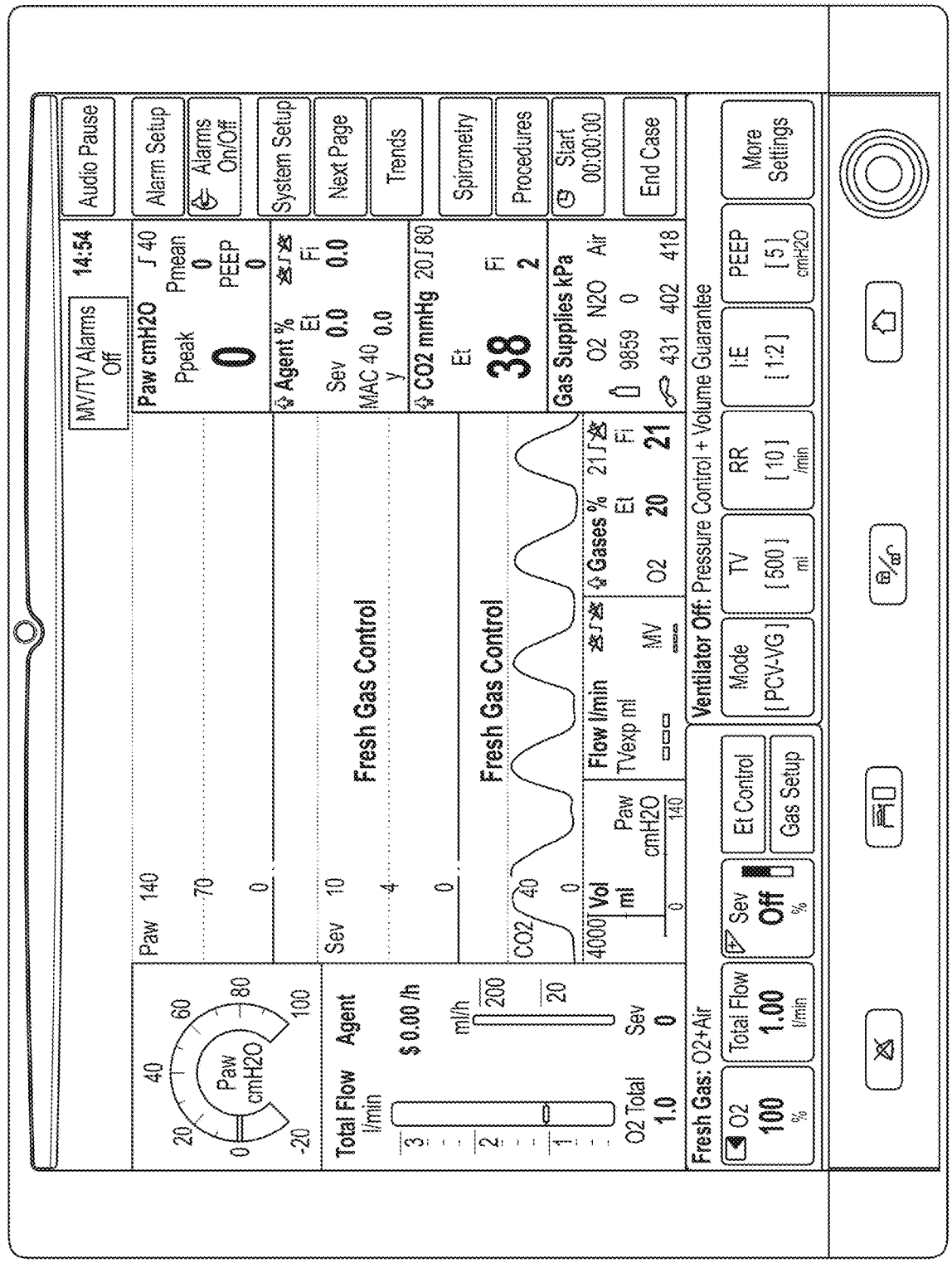
Figure 8D:
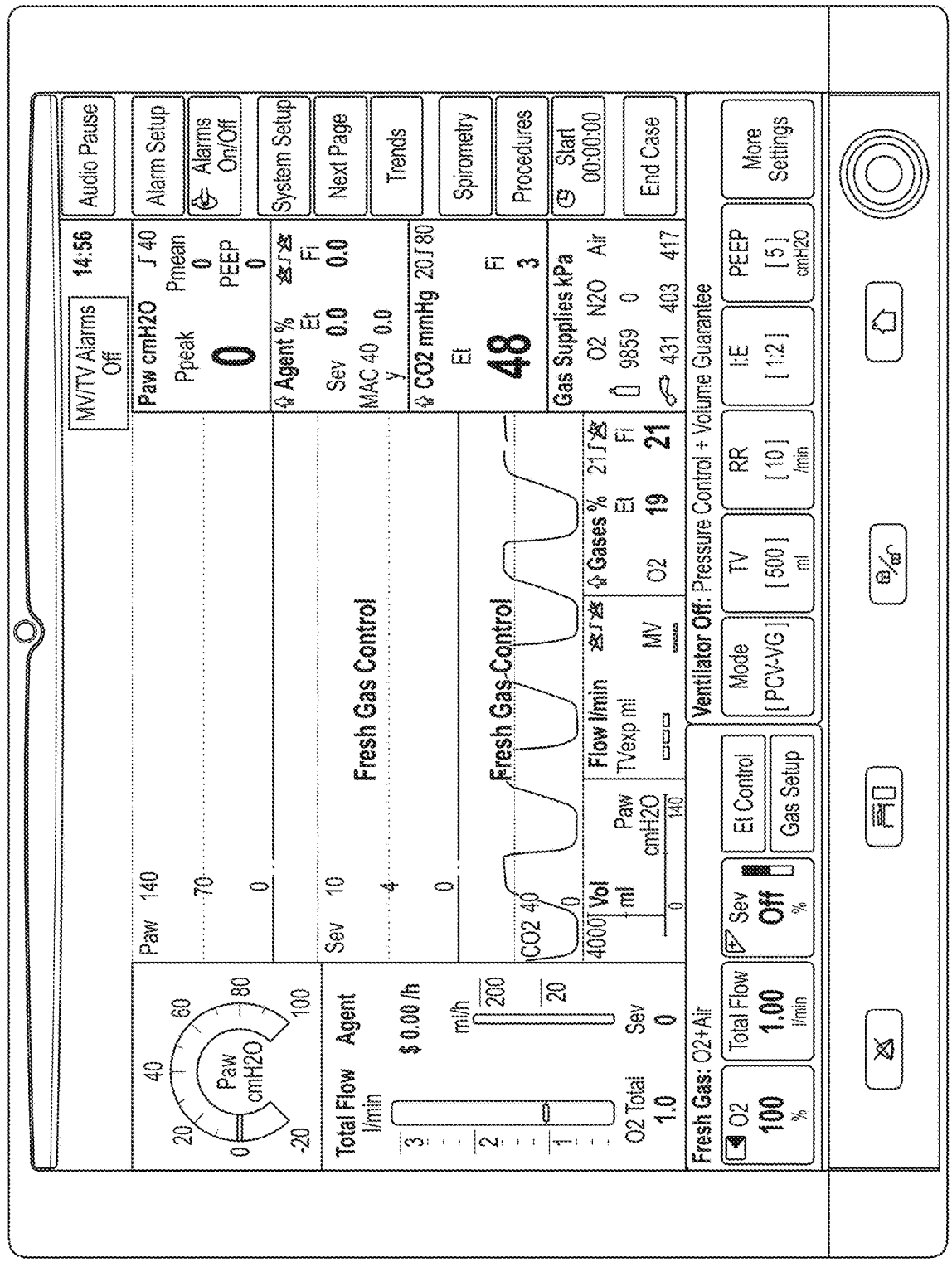
Figure 8E:
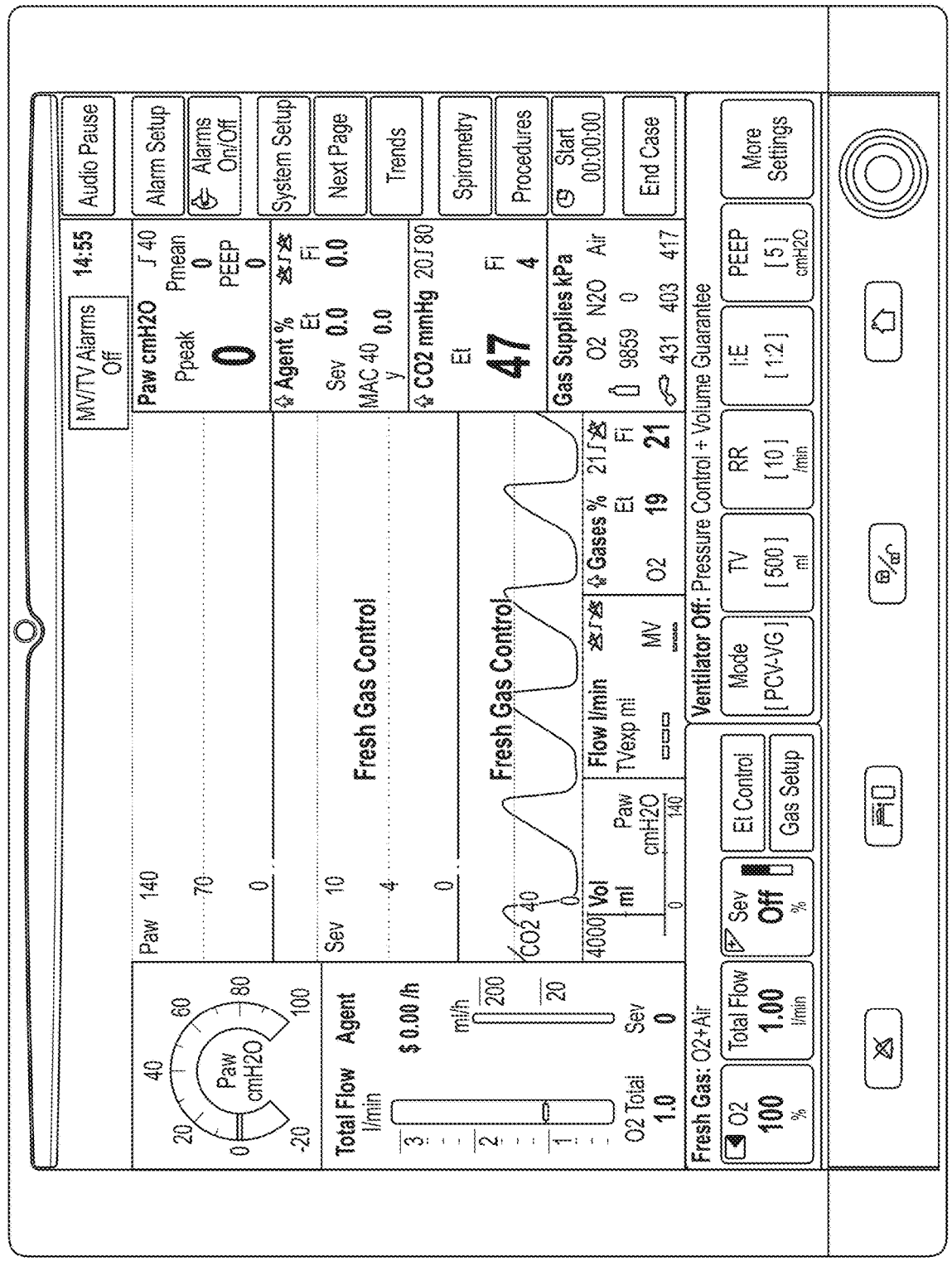

With reference to FIG. 6, an example GUI 51 of controller 19 is shown in the form of a display configured to be displayed on a touchscreen of the controller 19, or on a remote display in communication with controller 19, on which various patient characteristics can be displayed and altered, to allow the simulation to be set according to the training or simulation in question. The GUI in this example is split into a number of sub-displays, each indicative of a particular patient characteristic and/or any other relevant information. For example, there is a sub-display 51a indicative of $ETCO_2$ on a sliding scale. Adjustment of the slider on the sliding scale generates a control signal which is passed to device 1, such that the controller of device 1 controls the $CO_2$ output waveform accordingly. A further sub-display 51b is indicative of the wireless connection between controller 19 and device 1. Further sub-displays 51c-f are provided indicative of other patient vital signs including heart rate, $SpO_2$, blood pressure, and respiratory rate.

The GUI also enables selection of the particular $CO_2$ waveform provided by device 1. FIGS. 8b to 8e are images of four different example waveforms that can be generated, as per a standard anaesthetic machine.

Figure 9:
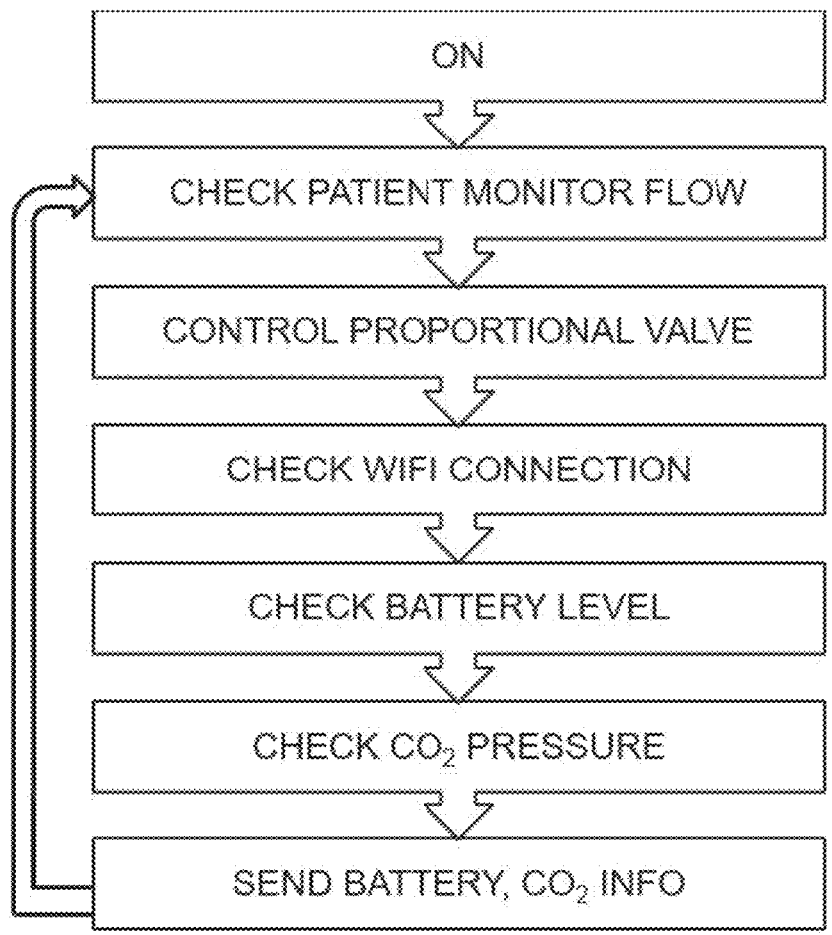
FIG. 9 shows firmware flow control steps of an expiratory breathing simulator device and medical simulation system in accordance with this disclosure.

With reference to FIG. 9, a device check protocol is schematically shown, showing various safety and device checks made periodically by the device 1.

Amongst the problems encountered in arriving at this disclosure, are
 1. Pressures within the $CO_2$ canisters are in excess of 1200 psi which made it difficult to regulate when the output pressure is in the tens of psi. Use of regulator 6 steps down the high inlet pressure to a useable pressure.
 3. Patient Monitors tend to suck at different flow rates with the consequence that it can be difficult to get the $ETCO_2$ Plateau at the correct value. This problem can be solved by sensing the Patient Monitor $CO_2$ level using flow meter 18 and then using a ratio to calculate the required $CO_2$ needed from the proportional valve 9 measured using flow meter 11.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Any discussion of the prior art throughout the specification should in no way be considered as an admission that such prior art is widely known or forms part of common general knowledge in the field.

The invention claimed is:

1. An expiratory breathing simulator device configured to simulate a real patient's expiratory breathing phase, the device comprising a housing comprising:
   a) a carbon dioxide ($CO_2$) Inlet configured to receive $CO_2$ from a $CO_2$ source;
   b) a $CO_2$ outlet from which a $CO_2$ flow exits the housing, the $CO_2$ outlet being configured to be connected to a medical monitoring apparatus;
   c) a $CO_2$ flow path through the housing from the $CO_2$ inlet to the $CO_2$ outlet;
   d) at least one sensor configured to measure a property of the $CO_2$ in the housing;
   e) a $CO_2$ adjuster configured to control the pressure and/or flow rate of $CO_2$ in the flow path using an output signal from the sensor;
   f) an air pump configured to deliver air into the flow of $CO_2$ in the flow path; and
   g) a controller configured to control the adjuster to control the $CO_2$ flow output from the $CO_2$ outlet such that the $CO_2$ flow has a desired or predetermined waveform; wherein
   the controller also controls the air pump to selectively deliver air into the $CO_2$ flow to prevent a value of End Tidal carbon dioxide ($ETCO_2$) being significantly greater than zero during inspiration.

2. The simulator device of claim 1 further comprising a $CO_2$ regulator configured to reduce the pressure of the $CO_2$ from the $CO_2$ source.

3. The simulator device of claim 1 wherein the sensor comprises a pressure sensor.

4. The simulator device of claim 1 wherein the $CO_2$ adjuster comprises a proportional valve.

5. The simulator device of claim 1 wherein the sensor comprises, or additionally comprises, a flow sensor or flow meter configured to generate an output indicative of the flow rate of the $CO_2$ flow in the $CO_2$ flow path.

6. The simulator device of claim 1 wherein the controller comprises one or more electronic data processors, and a wireless transceiver, configured to receive a $CO_2$ control signal from a further electronic device.

7. The simulator device of claim 1 wherein the housing is oblong and comprises a recessed portion on which the following connectors are provided, such that the connectors are recessed from the exterior of the housing:

a) a $CO_2$ input connector for connection to the $CO_2$ source; and
b) a $CO_2$ output connector for connection to a patient monitor or other medical device.

8. The simulator device of claim 1 comprising:
a) an ambient air inlet; and/or
b) an oxygen inlet, for optional connection to an oxygen supply.

9. The simulator device of claim 1 wherein the device housing comprises any one or more of:
a) a $CO_2$ pressure indicator, indicative of sufficient pressure being provided by the $CO_2$ source;
b) a connection indicator, indicative of the strength of any wireless connection with a remote electronic device;
c) a battery indicator, indicative of the charge state of the battery;
d) a power button, to activate or deactivate the device;
e) a $CO_2$ gauge.

10. A medical simulation system comprising:
a) the simulator device according to claim 1,
b) a vital signs simulator configured to simulate other vital signs of a patient; and
c) a simulation controller;
wherein the simulation controller is configured to generate a carbon dioxide ($CO_2$) control signal used by the simulator device to control the waveform of the $CO_2$ flow generated by the simulator device.

11. The system of claim 10 comprising a user interface configured to enable a user to adjust the $CO_2$ control signal.

12. The system of claim 11 wherein the user interface comprises a graphic user interface.

13. An expiratory breathing simulator method configured to simulate a real patient's expiratory breathing phase, the method comprising steps of:
a) receiving $CO_2$ in an inlet of an expiratory breathing simulator device from a $CO_2$ source;
b) controlling the pressure of $CO_2$ in a flow path through the device using a $CO_2$ adjuster of the device;
c) delivering a controlled flow of air into the flow of $CO_2$ in the flow path using an air pump;
d) using a controller to control the $CO_2$ adjuster to control the $CO_2$ flow output from a $CO_2$ outlet of the device to generate a $CO_2$ flow having a desired or predetermined waveform;
e) using a controller to control the air pump to deliver air into the $CO_2$ flow to prevent a value of End Tidal carbon dioxide ($ETCO_2$) being significantly greater than zero during inspiration.

* * * * *